United States Patent
Cleary et al.

(10) Patent No.: US 7,138,458 B2
(45) Date of Patent: *Nov. 21, 2006

(54) METHOD FOR PREPARING A TWO-PHASE WATER-ABSORBENT BIOADHESIVE COMPOSITION

(75) Inventors: Gary W. Cleary, Los Altos Hills, CA (US); Mikhail M. Feldstein, Moscow (RU); Valery G. Kulichikhin, Moscow (RU); Danir F. Bairamov, Moscow (RU)

(73) Assignees: Corium International, Inc., Redwood City, CA (US); A.V. Topchiev Institute of Petrochemical Synthesis, Russian Academy of Sciences, Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 10/964,431

(22) Filed: Oct. 12, 2004

(65) Prior Publication Data

US 2005/0049365 A1    Mar. 3, 2005

Related U.S. Application Data

(62) Division of application No. 10/137,196, filed on May 1, 2002, now Pat. No. 6,803,420.

(60) Provisional application No. 60/288,024, filed on May 1, 2001.

(51) Int. Cl.
*C08L 9/00* (2006.01)
*C08L 35/00* (2006.01)
*C08L 33/06* (2006.01)
*A61K 6/083* (2006.01)

(52) U.S. Cl. .............. 525/205; 525/206; 525/217; 525/218; 525/221; 525/222; 525/230; 525/232; 523/105

(58) Field of Classification Search ........... 525/205, 525/206, 217, 218, 221, 222, 230, 232; 523/105
See application file for complete search history.

(56) References Cited

U.S. PATENT DOCUMENTS

| | | | |
|---|---|---|---|
| 4,231,369 A | 11/1980 | Sørensen et al. | |
| 4,367,732 A | 1/1983 | Poulsen et al. | |
| 4,713,243 A | 12/1987 | Schiraldi et al. | |
| 4,867,748 A | 9/1989 | Samuelsen | |
| 5,240,995 A | 8/1993 | Gyory et al. | |
| 5,270,358 A | 12/1993 | Asmus | |
| 5,338,490 A | 8/1994 | Dietz et al. | |
| 5,633,010 A * | 5/1997 | Chen ...................... | 424/448 |
| 5,643,187 A | 7/1997 | Næstoft et al. | |
| 5,645,855 A | 7/1997 | Lorenz | |
| 5,663,010 A * | 9/1997 | Stocchiero ............... | 429/86 |
| 5,700,478 A | 12/1997 | Biegajski et al. | |
| 5,827,525 A | 10/1998 | Liao et al. | |
| 6,075,626 A | 6/2000 | Mizutani et al. | |
| 6,162,456 A | 12/2000 | Dunbar et al. | |
| 6,576,712 B1 | 6/2003 | Feldstein et al. | |
| 2003/0170308 A1* | 9/2003 | Cleary et al. ........... | 424/486 |
| 2003/0225356 A1* | 12/2003 | Kulichikhin et al. ...... | 602/54 |

FOREIGN PATENT DOCUMENTS

| | | |
|---|---|---|
| DE | 4219368 A1 | 12/1993 |
| EP | 0371421 B1 | 12/1994 |

* cited by examiner

*Primary Examiner*—Nathan M. Nutter
(74) *Attorney, Agent, or Firm*—Mintz, Levin, Cohn, Ferris, Glovsky and Popeo, P.C.

(57) ABSTRACT

A method is provided for preparing an adhesive composition that contains both a hydrophobic phase and a hydrophilic phase, wherein the hydrophobic phase is composed of a crosslinked hydrophobic polymer composition and the hydrophilic phase is a water-absorbent blend of a hydrophilic polymer and a complementary oligomer capable of crosslinking the hydrophilic polymer through hydrogen bonding, ionic bonding, and/or covalent bonding. The composition is useful as a bioadhesive, for affixing drug delivery systems, wound dressings, bandages, cushions, or the like to a body surface such as skin or mucosal tissue.

7 Claims, 4 Drawing Sheets

METHOD FOR PREPARING A TWO-PHASE WATER-ABSORBENT BIOADHESIVE COMPOSITION

CROSS-REFERENCE TO RELATED APPLICATIONS

This is a divisional of U.S. patent application Ser. No. 10/137,196, filed May 1, 2002, now U.S. Pat. No. 6,803,420, which claims priority under 35 U.S.C. § 119(e)(1) to provisional U.S. Patent Application Ser. No. 60/288,024, filed May 1, 2001 and application Ser. No. 10/137,196, filed May 1, 2002, now U.S. Pat. No. 6,803,420, issued on even date herewith.

TECHNICAL FIELD

This invention relates generally to adhesive compositions, and more particularly relates to a novel adhesive composition composed of a hydrophobic phase and a hydrophilic phase. The composition is useful as a bioadhesive in a variety of contexts involving application of a drug delivery system, wound dressing, cushion, or the like to an individual's skin or other body surface. The assignees of this application, Corium International, Inc. and the A.V. Topchiev Institute of Petrochemical Synthesis, Russian Academy of Sciences, are parties to a joint research agreement covering work in this and other fields.

BACKGROUND

Pressure-sensitive adhesives (PSAs) for application to the skin or other body surface are well known and have been used for many years in a variety of consumer and medical applications. Pressure-sensitive adhesives are characterized as being normally tacky and exhibiting instant tack when applied to a substrate. Many polymers have been used to manufacture pressure-sensitive adhesives as, for example, acrylic and methacrylic ester homo- or copolymers, butyl rubber-based systems, silicones, urethanes, vinyl esters and amides, olefin copolymer materials, natural or synthetic rubbers, and the like. All the PSAs are elastomers, i.e. they exhibit viscoelastic properties typical of rubbers.

Existing examples of pressure-sensitive adhesives used for affixing a drug delivery system, cushion, or the like to the skin include polysiloxanes (e.g., polydimethyl siloxanes, polydiphenyl siloxanes, and siloxane blends), polyisobutylenes, polyacrylates, acrylic acid-acrylate copolymers (e.g., copolymers of acrylic acid copolymers with 2-ethylhexyl acrylate or isooctyl acrylate), and tacky rubbers such as polyisobutene, polybutadiene, polystyrene-isoprene copolymers, polystyrene-butadiene copolymers, and neoprene (polychloroprene). All of these PSAs are hydrophobic polymers and their common disadvantage is a loss in adhesion toward hydrated substrates.

"Bioadhesion" is defined as a pressure-sensitive adhesion with respect to highly hydrated biological tissues such as mucosal tissue. In contrast to conventional pressure sensitive adhesives such as rubber, polysiloxanes, and acrylates that adhere mainly to dry substrates, bioadhesives (BAs) exhibit good tack when adhered to hydrated biological substrates. To be bioadhesive, water should provide a plasticizing effect on a polymer, i.e., the polymer should be hydrophilic. For example, the range of typical BAs includes slightly cross-linked polyacrylic and polymethacrylic acids (EP 0 371 421) as well as blends of hydrophilic cellulose derivatives (40–95%) with polyethylene glycol (PEG) (U.S. Pat. No. 4,713,243).

Bioadhesives become tacky as the crosslinked polymer swells in significant quantities of water. The cohesive strength of highly swollen hydrophilic polymers is generally low and the BAs thus differ from the PSAs in this regard.

Attempts to combine the properties of PSAs and BAs have been described by Biegajski et al. in U.S. Pat. No. 5,700,478, where a water-soluble pressure-sensitive mucoadhesive was obtained by blending 95–40% polyvinylpyrrolidone (PVP) with 0–50% hydroxypropyl cellulose (HPC) and 11–60% glycerol. Other examples of hydrophilic polymer blends coupling the properties of PSAs and BAs involve polyacrylic acid-polyvinyl alcohol (PAA-PVA) interpolymeric complexes formed by hydrogen bonding between the monomer units of the complementary polymer chains and plasticized with PEG-200, glycerol or polypropylene glycol (PPG), molecular weight 425 g/mol (German Patent Application No. DE 42 19 368).

The ideal performance characteristics of an adhesive composition intended for use on human skin and/or mucosal tissue present difficult and conflicting technical requirements. Initially, the adhesive should be suitable for long-term skin contact, and permeable to and physically and chemically compatible with any active agent and any permeation enhancers or other vehicles or additives that are present. The ideal adhesive should also be nonirritating, noncomedogenic and nonsensitizing, yet bond quickly to skin or mucosal tissue at the intended site of use with only very slight pressure. The adhesive should maintain its bond for as long a period of time as necessary and be resistant to inadvertent removal, yet be easily removed without removing any skin or leaving a residue (a suitable strength of an adhesive joint with the skin ranges from about 200 to 400 N/m under the 180 degree peel test). Furthermore, the adhesive composition should not be sensitive to or degradable by exposure to moisture or high humidity.

With bioadhesives, hydrophilic compositions are preferred for the adhesive compositions to adhere well to moist substrates. Hydrophilic adhesives are advantageous in other respects as well, insofar as:

(1) hydrophilic adhesives can provide greater adhesion compared with hydrophobic adhesives, because the surface energy of hydrophilic adhesives is typically higher and closer to that of biological substrates such as skin and mucosal membranes;

(2) hydrophilic adhesives are compatible with a wide variety of drugs, excipients and additives;

(3) the plasticizing effect of water sorbed by hydrophilic adhesives from hydrated skin or mucosal tissues enhances adhesion, in contrast to hydrophobic adhesives;

(4) the enhanced solubility of drugs in hydrophilic adhesives facilitates control over drug release kinetics;

(5) with hydrophilic adhesives, based on hydrophilic polymers, there is an expanded capability to control and manipulate the adhesive-cohesive balance; and (6) the adhesive properties of hydrophilic polymers are considerably less sensitive to their molecular weight than those of hydrophobic polymers, as a result of specific intramolecular and intermolecular interaction within hydrophilic adhesives.

In order to increase the hydrophilicity of an adhesive composition, hydrophobic PSAs have been "hydrophilized" by incorporation of non-tacky hydrophilic polymers and fillers into a hydrophobic adhesive. Thus, polyisobutylene (PIB) PSA has been hydrophilized by incorporation of cellulose and cellulose derivatives (U.S. Pat. No. 4,231,369), polyvinyl alcohol (PVA), pectin and gelatin (U.S. Pat. Nos. 4, 367,732 and 4,867,748), and $SiO_2$ (U.S. Pat. No.

5,643,187). Rubber adhesives have also been modified by filling with amphiphilic surfactants, or by treating the PSA polymer with a plasma-oxygen discharge. Acrylic PSAs can be hydrophilized by incorporation of PVP (U.S. Pat. No. 5,645,855). Hydrophilization of hydrophobic adhesives, while somewhat effective, tends to result in a partial loss of adhesion.

There is, accordingly, a need in the art for improved bioadhesive compositions that combine the properties of hydrophobic PSAs with the many advantages of hydrophilic adhesive compositions. It would also be ideal if such an adhesive composition could be adapted for a variety of uses, e.g., in wound healing and bandages, in the fabrication of transdermal and other drug delivery systems, in preparing medicated adhesive formulations for topical and transdermal pharmaceutical formulations, in pressure-relieving cushions (which may or may not be medicated), as sealants for ostomy devices and prostheses, as conductive adhesives for attachment of electroconductive articles such as electrodes to the skin, and the like.

SUMMARY OF THE INVENTION

It is a primary object of the invention to provide a novel adhesive composition that meets all of the above-discussed needs in the art.

In one embodiment, the invention pertains to a two-phase, water-absorbent adhesive composition that comprises a blend of a hydrophobic pressure-sensitive adhesive with a water-absorbent hydrophilic composition. As such, the composition comprises a hydrophobic phase and a hydrophilic phase, wherein the hydrophobic phase includes a hydrophobic polymer, e.g., a crosslinked hydrophobic polymer, preferably a hydrophobic PSA, and the hydrophilic phase comprises a blend of a relatively high molecular weight hydrophilic polymer and a lower molecular weight complementary oligomer that is capable of crosslinking the hydrophilic polymer through hydrogen bonds, and optionally through covalent and/or ionic bonds as well. The weight ratio of the hydrophilic polymer to the complementary oligomer is selected to optimize the adhesive strength, cohesive strength, and hydrophilicity of the composition. The composition may additionally include any number of additives, e.g., active agents, fillers, tackifiers, and the like.

In another embodiment, a drug delivery system is provided comprising an active agent in an adhesive composition as described above, wherein the system has a body-contacting surface and an outer surface, with the adhesive composition present within a region of the body-contacting surface. The body-contacting surface may be entirely comprised of the adhesive composition, or the perimeter of the body-contacting surface may be composed of a different skin contact adhesive. The drug delivery system may be designed for systemic delivery of an active agent, e.g., via the transdermal or transmucosal routes. The system may also be designed for topical administration of a locally active agent.

In a related embodiment, a wound dressing is provided comprised of a substrate for application to the wound region, wherein the substrate has a body-contacting surface and an outer surface, with the adhesive composition present in a wound-contacting region of the body-contacting surface. As with drug delivery systems, the body-contacting surface may be entirely comprised of the adhesive composition, although it is preferred that the composition be present in a central region on the body-contacting surface, with the perimeter of the body-contacting surface composed of a different skin contact adhesive. In this embodiment, absorption of water present in the wound exudate gradually causes the wound dressing to lose tack.

The adhesive compositions herein are also useful in a host of additional applications, e.g., in various types of pharmaceutical formulations, pressure-relieving cushions (which may or may not be medicated), bandages, ostomy devices, prosthesis securing means, face masks, sound, vibration or impact absorbing materials, and the like. Also, the compositions may be rendered electrically conductive by incorporation of an electrically conductive material, and may thus be used for attaching an electroconductive article, such as an electrode (e.g., a transcutaneous electric nerve stimulation, or "TENS" electrode, an electrosurgical return electrode, or an EKG monitoring electrode), to an individual's body surface.

The adhesive compositions of the invention provide a number of significant advantages relative to the prior art. In particular, the present compositions:

(1) may be fabricated so as to display very high swelling upon contact with water without concomitant loss of adhesion;

(2) can be fabricated so as to exhibit little or no cold flow during use;

(3) are useful and versatile bioadhesives in a number of contexts, including wound dressings, active agent delivery systems for application to a body surface, pressure-relieving cushions, and the like; and (4) are readily modified during manufacture so that properties such as adhesive strength, cohesive strength, absorption, and swelling can be optimized.

DETAILED DESCRIPTION OF THE INVENTION

Figure 1:
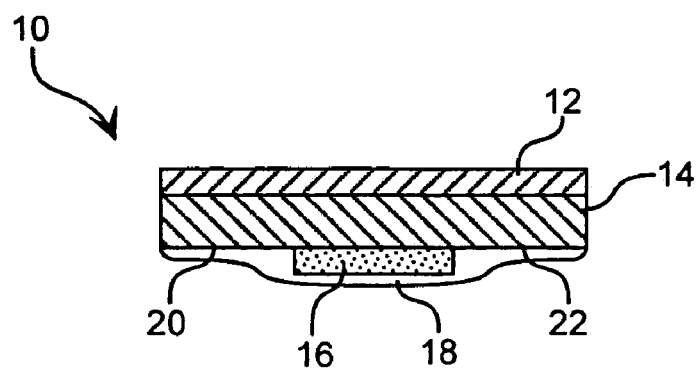
FIG. 1 schematically illustrates one embodiment of a wound dressing prepared with an adhesive composition of the invention, wherein the dressing is composed of an outwardly facing backing layer and a body-facing skin contact adhesive layer laminated thereto, wherein an adhesive composition of the invention is present as a film on an interior region of the body-contacting surface of the skin contact adhesive layer.

I. Definitions and Nomenclature:

Before describing the present invention in detail, it is to be understood that unless otherwise indicated this invention is not limited to specific compositions, components or manufacturing processes, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise. Thus, for example, reference to "a hydrophilic polymer" includes not only a single hydrophilic polymer but also a combination or mixture of two or more different hydrophilic polymers, reference to "a plasticizer" includes a combination or mixture of two or more different plasticizers as well as a single plasticizer, and reference to "a hydrophobic pressure-sensitive adhesive" includes a mixture of two or more such adhesives as well as a single such adhesive, and the like.

In describing and claiming the present invention, the following terminology will be used in accordance with the definitions set out below.

The definitions of "hydrophobic" and "hydrophilic" polymers are based on the amount of water vapor absorbed by polymers at 100% relative humidity. According to this classification, hydrophobic polymers absorb only up to 1 wt. % water at 100% relative humidity ("rh"), while moderately hydrophilic polymers absorb 1–10% wt. % water, hydrophilic polymers are capable of absorbing more than 10 wt. % of water, and hygroscopic polymers absorb more than 20 wt. % of water.

The term "crosslinked" herein refers to a composition containing intramolecular and/or intermolecular crosslinks, whether arising through covalent or noncovalent bonding. "Noncovalent" bonding includes both hydrogen bonding and electrostatic (ionic) bonding.

The term "polymer" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

The term "water-insoluble" refers to a compound or composition whose solubility in water is less than 5 wt. %, preferably less than 3 wt. %, more preferably less than 1 wt. % (measured in water at 20° C.).

The term "active agent" is used herein to refer to a chemical material or compound suitable for administration to a human patient and that induces a desired beneficial effect, e.g., exhibits a desired pharmacological activity. The term includes, for example, agents that are therapeutically effective, prophylactically effective, and cosmetically (and cosmeceutically) effective. Also included are derivatives and analogs of those compounds or classes of compounds specifically mentioned which also induce the desired beneficial effect.

By "transdermal" drug delivery is meant administration of a drug to the skin surface of an individual so that the drug passes through the skin tissue and into the individual's blood stream. Unless otherwise indicated, the term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of an active agent to a body surface such as the skin or mucosa, as in, for example, topical drug administration in the prevention or treatment of various skin disorders, the application of cosmetics and cosmeceuticals (including moisturizers, masks, sunscreens, etc.), and the like. Topical administration, in contrast to transdermal administration, provides a local rather than a systemic effect.

The term "body surface" is used to refer to any surface located on the human body or within a body orifice. Thus, a "body surface" includes, by way of example, skin, or mucosal tissue, including the interior surface of body cavities that have a mucosal lining. Unless otherwise indicated, the term "skin" as used herein should be interpreted as including mucosal tissue and vice versa.

Similarly, when the term "transdermal" is used herein, as in "transdermal drug administration" and "transdermal drug delivery systems," it is to be understood that unless explicitly indicated to the contrary, both "transmucosal" and "topical" administration and systems are intended as well.

II. Adhesive Compositions:

In a first embodiment, an adhesive composition is provided that combines the properties of a hydrophobic PSA with the advantages of a hydrophilic adhesive composition. The composition is comprised of a hydrophobic phase and a hydrophilic phase, wherein the hydrophobic phase includes at least one hydrophobic polymer, and the hydrophilic phase, dispersed or otherwise contained therein, is comprised of a mixture of a hydrophilic polymer and a low molecular weight complementary oligomer capable of hydrogen bonding thereto. The low molecular weight complementary oligomer may also serve to crosslink the hydrophilic polymer via ionic and/or covalent bonding.

A. The Hydrophobic Phase

The hydrophobic phase is comprised of at least one hydrophobic polymer. The hydrophobic polymer is typically a hydrophobic pressure-sensitive adhesive polymer, preferably a thermosetting polymer. Preferred hydrophobic PSA polymers are crosslinked butyl rubbers, wherein a "butyl rubber," as well known in the art, is an isoprene-isobutylene copolymer typically having an isoprene content in the range of about 0.5 to 3 wt. %, or a vulcanized or modified version thereof, e.g., a halogenated (brominated or chlorinated) butyl rubber. In a particularly preferred embodiment, the hydrophobic PSA polymer is butyl rubber crosslinked with polyisobutylene. Other suitable hydrophobic polymers include, for example, natural rubber adhesives, vinyl ether polymers, polysiloxanes, polyisoprene, butadiene acrylonitrile rubber, polychloroprene, atactic polypropylene, and ethylene-propylene-diene terpolymers (also known as "EPDM" or "EPDM rubber") (available as Trilene® 65 and Trilene® 67 from Uniroyal Chemical Co., Middlebury, Conn.). Still other suitable hydrophobic PSAs will be known to those of ordinary skill in the art and/or are described in the pertinent texts and literature. See, for example, the *Handbook of Pressure-Sensitive Adhesive Technology*, 2nd Ed., Satas, Ed. (New York: Von Nostrand Reinhold, 1989). Particularly preferred hydrophobic polymers are the crosslinked butyl rubbers available in the Kalar® series from Elementis Specialties, Inc. (Hightstown, N.J.), with Kalar® 5200, Kalar® 5215, Kalar® 5246, and Kalar® 5275 most preferred.

For most applications, the crosslinked hydrophobic polymer should have a sufficiently high degree of crosslinking so that the composition does not exhibit cold flow following application to a surface, e.g. a body surface such as skin. As will be appreciated by those in the art, the degree of crosslinking correlates with Mooney viscosity, a measure of the resistance of a raw or unvulcanized rubber to deformation as measured in a Mooney viscometer. A higher Mooney viscosity indicates a higher degree of crosslinking. The Mooney viscosity of preferred hydrophobic PSAs for use herein should be at least 20 cps at 25° C., and will generally be in the range of about 25 cps to 80 cps, preferably about 30 cps to 75 cps, at 25° C. The Mooney viscosities of the preferred Kalar® series polymers herein are as follows: Kalar® 5200, 40–45 cps; Kalar® 5215, 47–57 cps; Kalar® 5246, 30–40 cps; and Kalar® 5275, 70–75 cps (all at 25° C.).

The molecular weight of the hydrophobic PSA is not critical, although the molecular weight will typically be less than about 100,000 Da. The amount of the polymer generally, although not necessarily, represents in the range of about 5 wt. % to 15 wt. %, preferably about 7.5 wt. % to 12 wt. %, most preferably about 7.5 wt. % to 10 wt. %, of the composition after drying.

Other hydrophobic polymers that may be used in place of or in addition to the hydrophobic PSA include, without limitation, hydrocarbon polymers such as polyethylene, acrylate polymers and copolymers, polyacrylamides, polyurethanes, plasticized ethylene-vinyl acetate copolymers, polyisobutylenes, polybutadiene, and neoprene (polychloroprene). Additional hydrophobic polymers suitable for incorporation into the hydrophobic phase are natural and synthetic elastomeric polymers, including, for example, AB, ABA, and "multiarmed" $(AB)_x$ block copolymers, where for example, A is a polymerized segment or "block" comprising aryl-substituted vinyl monomers, preferably styrene, α-methyl styrene, vinyl toluene, and the like, B is an elastomeric, conjugated polybutadiene or polyisoprene block, and x has a value of 3 or more. Preferred elastomers are butadiene-based and isoprene-based polymers, particularly styrene-butadiene-styrene (SBS), styrene-butadiene (SB), styrene-isoprene-styrene (SIS), and styrene-isoprene (SI) block copolymers, where "S" denotes a polymerized segment or "block" of styrene monomers, "B" denotes a polymerized segment or block of butadiene monomers, and "I" denotes a polymerized segment or block of isoprene monomers. Other suitable elastomers include radial block copolymers having a SEBS backbone (where "E" and "B" are, respectively, polymerized blocks of ethylene and butylene) and I and/or SI arms. Natural rubber (polyisoprene) and synthetic polyisoprene can also be used.

Commercially available hydrophobic elastomers include linear SIS and/or SI block copolymers such as Quintac® 3433 and Quintac® 3421, available from Nippon Zeon Company, Ltd. (U.S. sales office—Louisville, Ky.); Vector® DPX 559, Vector® 4111 and Vector® 4113, available from Dexco, a partnership of Exxon Chemical Co. (Houston, Tex.) and Dow Chemical Co. (Midland Mich.); and Kraton® rubbers, such as Kraton 604x, Kraton D-1107, Kraton D-1117, and Kraton D-1113, available from Shell Chemical Co. (Houston, Tex.). Kraton D-1107 is a predominantly SIS elastomer containing about 15% by weight SI blocks. Kraton D-1320x is an example of a commercially available $(SI)_xI_y$ multiarmed block copolymer in which some of the arms are polyisoprene blocks. Commercially available butadiene-based elastomers include SBS and/or SB rubbers, such as Kraton D-1101, D-1102 and D-1118X, from Shell Chemical Co.; Solprene® 1205, an SB block copolymer available from Housemex, Inc. (Houston, Tex.); and Kraton TKG-101 (sometimes called "Tacky G"), a radial block copolymer having an SEBS backbone (E=ethylene block; B=butylene block) and I and/or SI arms.

In a particularly preferred embodiment, the hydrophobic phase is comprised of a butyl rubber, i.e., an isoprene-isobutylene copolymer typically having an isoprene content in the range of about 0.5 to 3 wt. %, crosslinked with polyisobutylene. Crosslinking may be effected using curing processes known to those of ordinary skill in the art and/or described in the pertinent texts and literature, e.g., using radiation, chemical crosslinking, and/or heat. However, a preferred process involves mixing the polyisobutylene and the butyl rubber at a temperature in the range of about 80° C. to about 140° C., followed by a thermal cure at a higher temperature, generally in the range of about 150° C. to about 170° C., in the presence of a suitable curing agent and an organic peroxide or zinc oxide in combination with zinc stearate or stearic acid. Preferably, the reaction is carried out in the presence of an organic peroxide. Suitable organic peroxides are generally selected from: dialkyl peroxides such as t-butyl peroxide and 2,2-bis(t-butylperoxy)propane; diacyl peroxides such as benzoyl peroxide and acetyl peroxide; peresters such as t-butyl perbenzoate and t-butyl per-2-ethylhexanoate; perdicarbonates such as dicetyl peroxy dicarbonate and dicyclohexyl peroxy dicarbonate; ketone peroxides such as cyclohexanone peroxide and methylethylketone peroxide; and hydroperoxides such as cumene hydroperoxide and tert-butyl hydroperoxide. Curing agents for this process are those compounds known in the art as vulcanizing agents for butyl rubber, and thus include, without limitation, alkyl phenol-formaldehyde resins, dicatechol borate salts (e.g., Permalux®, the di-ortho-tolylguanidine salt of dicatechol borate), (m-phenylene bis maleimide, 2,4,6-trimercapto-5 triazine), zinc diethyl dithiocarbamate and other dithiocarbamates, thiuram sulfides (e.g., Tetrone® A, dipentamethylene thiuram hexasulfide; and "TMTDS,"

tetramethyl thiuram disulfide) preferably in combination with sulfur, alkylated phenol disulfides, and diphenyl phenylene diamine (DPPD).

Preferred curing agents for the aforementioned process are alkyl phenol-formaldehyde condensation resins. Such resins may be halogenated, in which case the terminal methylol moieties of the resin are halogenated, such that a halomethyl (e.g., a bromomethyl or chloromethyl) group is present at each terminus. These resins are ideal curing agents, insofar as the curing reaction is not accompanied by formation of any volatile organic compounds. These resins have the molecular structure

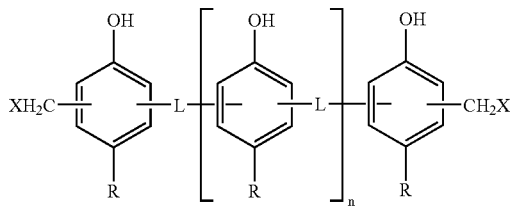

wherein n is typically an integer in the range of zero to 10 inclusive, X is hydroxyl or halo (typically bromo or chloro), R is an alkyl group, generally having 1 to 10 carbon atoms, and L is a lower alkylene or lower oxyalkylene linking group, preferably —$CH_2$— or —$CH_2$—O—$CH_2$—. Methylol-terminated compounds, wherein X is hydroxyl, are commercially available as, for example, TACKIROL 201 (trade name, a product of Taoka Chemical Co., Ltd.) and HITANOL 2501 (trade name, a product of Hitachi Chemical Co., Ltd), while the dibromomethyl analog is available as SP1055 from Schenectady Chemical Company.

B. The Hydrophilic Phase

The hydrophilic phase comprises a blend of a hydrophilic polymer and a complementary oligomer capable of crosslinking the hydrophilic polymer through hydrogen bonds, ionic bonds, and/or covalent bonds. Suitable hydrophilic polymers include repeating units derived from an N-vinyl lactam monomer, a carboxy vinyl monomer, a vinyl ester monomer, an ester of a carboxy vinyl monomer, a vinyl amide monomer, and/or a hydroxy vinyl monomer. Such polymers include, by way of example, poly(N-vinyl lactams), poly(N-vinyl acrylamides), poly(N-alkylacrylamides), substituted and unsubstituted acrylic and methacrylic acid polymers, polyvinyl alcohol (PVA), polyvinylamine, copolymers thereof and copolymers with other types of hydrophilic monomers (e.g. vinyl acetate).

Poly(N-vinyl lactams) useful herein are preferably non-crosslinked homopolymers or copolymers of N-vinyl lactam monomer units, with N-vinyl lactam monomer units representing the majority of the total monomeric units of a poly(N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valerolactam; and N-vinyl-2-caprolactam. Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly (N-alkylacrylamides) include, by way of example, poly(methacrylamide) and poly(N-isopropyl acrylamide)(P-NIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly polyvinyl pyrrolidone (PVP) and poly(N-vinyl caprolactam) (PVCap); poly(N-vinyl acetamides), particularly polyacetamide per se; polymers of carboxy vinyl monomers, particularly polyacrylic acid and polymethacrylic acid; and copolymers and blends thereof. PVP and PVCap are particularly preferred.

The molecular weight of the hydrophilic polymer is not critical; however, the number average molecular weight of the hydrophilic polymer is generally in the range of approximately 20,000 to 2,000,000, more typically in the range of approximately 200,000 to 1,000,000.

The oligomer is "complementary" to the hydrophilic polymers in that it is capable of hydrogen bonding thereto. Preferably, the complementary oligomer is terminated with hydroxyl groups, amino or carboxyl groups. The oligomer typically has a glass transition temperature $T_g$ in the range of about –100° C. to about –30° C. and a melting temperature $T_m$ lower than about 20° C. The oligomer may be also amorphous. The difference between the $T_g$ values the hydrophilic polymer and the oligomer is preferably greater than about 50° C., more preferably greater than about 100° C., and most preferably in the range of about 150° C. to about 300° C. The hydrophilic polymer and complementary oligomer should be compatible, i.e. capable of forming a homogeneous blend that exhibits a single $T_g$, intermediate between those of the unblended components. Generally, the oligomer will have a molecular weight in the range from about 45 to about 800, preferably in the range of about 45 to about 600. Examples of suitable oligomers include, but are not limited to, low molecular weight polyalcohols (e.g. glycerol), oligoalkylene glycols such as ethylene glycol and propylene glycol, ether alcohols (e.g., glycol ethers), alkane diols from butane diol to octane diol, including carboxyl-terminated and amino-terminated derivatives of polyalkylene glycols. Polyalkylene glycols, optionally carboxyl-terminated, are preferred herein, and polyethylene glycol having a molecular weight in the range of about 300 to 600 is an optimal complementary oligomer.

The hydrophilic polymer and the complementary oligomer should be miscible with respect to each other and have disparate chain lengths (as may be deduced from the above). The ratio of the weight average molecular weight of the hydrophilic polymer to that of the oligomer should be within about 200 and 200,000, preferably within about 1,250 and 20,000. Also, the polymer and the oligomer should contain complementary functional groups capable of hydrogen bonding, ionically bonding, or covalently bonding to each other. Ideally, the complementary functional groups of the polymer are located throughout the polymeric structure, while the functional groups of the oligomer are preferably located at the two termini of a linear molecule, and are not present along the backbone. Forming hydrogen bonds or ionic bonds between the two terminal functional groups of the oligomer and the corresponding functional groups contained along the backbone of the hydrophilic polymer results in a noncovalently linked supramolecular network.

As discussed in co-pending application Ser. No. 09/900, 697 for "Preparation of Hydrophilic Pressure Sensitive Adhesives Having Optimized Adhesive Properties," filed on Jul. 6, 2001 (published as U.S. Patent Publication No. 2002/0037977 on Mar. 28, 2002), the ratio of the hydrophilic polymer to the complementary oligomer in the aforementioned blend affects both adhesive strength and the cohesive strength. As explained in the aforementioned patent application, the complementary oligomer decreases the glass transition of the hydrophilic polymer/complementary oligomer blend to a greater degree than predicted by the Fox equation, which is given by equation (1)

$$\frac{1}{T_{g\ predicted}} = \frac{w_{pol}}{T_{g\ pol}} + \frac{w_{pl}}{T_{g\ pl}} \quad (1)$$

where $T_{g\ predicted}$ is the predicted glass transition temperature of the hydrophilic polymer/complementary oligomer blend, $w_{pol}$ is the weight fraction of the hydrophilic polymer in the blend, $w_{pl}$ is the weight fraction of the complementary oligomer in the blend, $T_{g\ pol}$ is the glass transition temperature of the hydrophilic polymer, and $T_{g\ pl}$ is the glass transition temperature of the complementary oligomer. As also explained in that patent application, an adhesive composition having optimized adhesive and cohesive strength can be prepared from a hydrophilic polymer and a complementary oligomer by selecting the components and their relative amounts to give a predetermined deviation from $T_{g\ predicted}$. Generally, to maximize adhesion, the predetermined deviation from $T_{g\ predicted}$ will be the maximum negative deviation, while to minimize adhesion, any negative deviation from $T_{g\ predicted}$ is minimized. Optimally, the complementary oligomer represents approximately 25 wt. % to 75 wt. %, preferably about 30 wt. % to about 60 wt. %, of the hydrophilic polymer/complementary oligomer blend, and, correspondingly, the hydrophilic polymer represents approximately 75 wt. % to 25 wt. %, preferably about 70 wt. % to about 40 wt. %, of the hydrophilic polymer/oligomer blend.

Another general predictor of pressure-sensitive adhesive behavior in polymers is the $\Delta C_p T_g$ product, where $\Delta C_p$ is the change in heat capacity at the polymer transition point from the glassy to the viscoelastic state. This product features a measure of the amount of heat that has to be expended in order to provide the polymer transition from the glassy to the viscoelastic state and to impart translational mobility to polymeric segments. As the hydrophilic polymer, e.g., polyvinyl pyrrolidone, is mixed with the complementary oligomer, e.g., PEG-400 occurs, the $\Delta C_p T_g$ product decreases, passing through a minimum that corresponds to the maximum in adhesion. It is the product $\Delta C_p T_g$ which sets the PSAs apart from non-adhesive polymers (Table 1). The $\Delta C_p T_g$ values, which are associated with the adhesive PVP-PEG blends and hydrophobic PSA's (PDMS, PIB and natural rubber), are notably grouped within a narrow area ranging from 45.0 to 92.0 J/g, predominantly near 65–80 J/g. Non-adhesive polymers exhibit higher $\Delta C_p T_g$ values.

TABLE 1

Glass transition characteristics of representative polymers.

| Polymer | Tg, K | ΔCp, J/gK | ΔCpTg J/g |
|---|---|---|---|
| Polydimethylsiloxane | 150 | 0.30 | 45.0 |
| Polyisobuthylene | 200 | 0.40 | 79.6 |
| Natural rubber | 200 | 0.46 | 92.0 |
| Polyethylene | 237 | 0.39 | 92.5 |
| PEG-400 | 200 | 0.51 | 101.4 |
| Bisphenol polycarbonate | 415 | 0.25 | 103.9 |
| Polymethyl methacrylate | 385 | 0.29 | 112.8 |
| Poly(N-vinyl pyrrolidone) | 449 | 0.27 | 121.2 |
| Polypropylene | 253 | 0.55 | 139.2 |
| Polystyrene | 375 | 0.38 | 141.0 |
| Polyvinyl acetate | 305 | 0.50 | 153.4 |
| Polyethylene terephthalate | 340 | 0.49 | 165.7 |
| Polyvinyl chloride | 355 | 0.63 | 229.9 |

The $\Delta C_p T_g$ value outlines a subtle balance between free volume and cohesive interactions energy in polymers (Feldstein et al. (1999), *Polym Mater. Sci. Eng.* 81:467–468). In general, the enhanced free volume has to be counterbalanced by a high attractive interaction energy in order for adhesion to appear. Enhanced free volume results in high molecular mobility and liquid-like fluidity of a PSA polymer, whereas substantial cohesive interaction energy provides cohesive toughness and rubber-like resistance to flow.

For certain applications, particularly when high cohesive strength is desired (such as with pressure-relieving cushions), the hydrophilic polymer and optionally the complementary oligomer should be covalently crosslinked. The hydrophilic polymer may be covalently crosslinked, either intramolecularly or intermolecularly, and/or the hydrophilic polymer and the complementary oligomer may be covalently crosslinked. In the former case, there are no covalent bonds linking the hydrophilic polymer to the complementary oligomer, while in the latter case, there are covalent crosslinks binding the hydrophilic polymer to the complementary oligomer. The hydrophilic polymer, or the hydrophilic polymer and the complementary oligomer, may be covalently crosslinked using heat, radiation, or a chemical curing (crosslinking) agent. The degree of crosslinking should be sufficient to eliminate or at least minimize cold flow under compression.

For covalently crosslinked hydrophilic polymer/complementary oligomer systems, the oligomer should be terminated at each end with a group capable of undergoing reaction with a functional group on the hydrophilic polymer. Such reactive groups include, for example, hydroxyl groups, amino groups, and carboxyl groups. These difunctionalized oligomers may be obtained commercially or readily synthesized using techniques known to those of ordinary skill in the art and/or described in the pertinent texts and literature.

For thermal crosslinking, a free radical polymerization initiator is used, and can be any of the known free radical-generating initiators conventionally used in vinyl polymerization. It has now been found that incorporation of an acrylate-type curing agent typically used for photochemical curing is also advantageous in the thermal crosslinking of the hydrophilic polymer/complementary oligomer blend. Such agents include, by way of example, 1,4-butylene di-methacrylate or -acrylate; ethylene di-methacrylate or -acrylate; trimethylolpropane di- or tri-acrylate; glyceryl di-acrylate or -methacrylate; glyceryl tri-acrylate or -methacrylate; glycidyl acrylate or methacrylate; pentaerythritol triacrylate or trimethacrylate; diallyl phthalate; 2,2-bis(4-methacryloxyphenyl)propane; diallyl adipate; di(2-acryloxyethyl) ether; dipentaerythritol monohydroxypentaacrylate; neopentyl glycol diacrylate or dimethacrylate;

polypropylene glycol diacrylate or dimethacrylate; and 1,3,5-tri-(2-methacryloxyethyl)-s-triazine; and hexamethylene diacrylate or dimethacrylate.

Preferred initiators for thermal crosslinking are organic peroxides and azo compounds, generally used in an amount from about 0.01 wt. % to 15 wt. %, preferably 0.05 wt. % to 10 wt. %, more preferably from about 0.1 wt. % to about 5% and most preferably from about 0.5 wt. % to about 4 wt. % of the polymerizable material. Suitable organic peroxides include those described above with respect to agents used in connection with curing butyl rubber, i.e., dialkyl peroxides such as t-butyl peroxide and 2,2 bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds include azo bis (isobutyronitrile) and azo bis (2,4-dimethylvaleronitrile). The temperature for thermal crosslinking will depend on the actual components and may be readily deduced by one of ordinary skill in the art, but typically ranges from about 80° C. to about 200° C.

Crosslinking may also be accomplished with radiation, typically in the presence of a photoinitator. The radiation may be ultraviolet, alpha, beta, gamma, electron beam, and x-ray radiation, although ultraviolet radiation is preferred. Useful photosensitizers are triplet sensitizers of the "hydrogen abstraction" type, and include benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylacetophenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthones such as 2-isopropylthioxanthone, 2-chlorothio-xanthone, 2,4 dimethyl thioxanone, 2,4 dichlorothioxanone, and 2,4-diethyl thioxanone, and acyl phosphine oxides. Other crosslinking agents suitable for effecting photocuring include, without limitation, 1,4-butylene dimethacrylate or -acrylate; ethylene di-methacrylate or -acrylate; trimethylolpropane di- or tri-acrylate; glyceryl di-acrylate or -methacrylate; glyceryl tri-acrylate or -methacrylate; glycidyl acrylate or methacrylate; pentaerythritol triacrylate or trimethacrylate; diallyl phthalate; 2,2-bis(4-methacryloxyphenyl)-propane; diallyl adipate; di(2-acryloxyethyl) ether; dipentaerythritol monhydroxypentaacrylate; neopentyl glycol diacrylate or dimethacrylate; polypropylene glycol diacrylate or dimethacrylate; and 1,3,5-tri-(2-methacryloxyethyl)-s-triazine; hexamethylene diacrylate or dimethacrylate. Radiation having a wavelength of 200 to 800 nm, preferably, 200 to 500 nm, is preferred for use herein, and low intensity ultraviolet light is sufficient to induce crosslinking in most cases. However, with photosensitizers of the hydrogen abstraction type, higher intensity UV exposure may be necessary to achieve sufficient crosslinking. Such exposure can be provided by a mercury lamp processor such as those available from PPG, Fusion, Xenon, and others. Crosslinking may also be induced by irradiating with gamma radiation or an electron beam. Appropriate irradiation parameters, i.e., the type and dose of radiation used to effect crosslinking, will be apparent to those skilled in the art.

Suitable chemical curing agents, also referred to as chemical cross-linking "promoters," include, without limitation, polymercaptans such as 2,2-dimercapto diethylether, dipentaerythritol hexa(3-mercaptopropionate), ethylene bis(3-mercaptoacetate), pentaerythritol tetra(3-mercaptopropionate), pentaerythritol tetrathioglycolate, polyethylene glycol dimercaptoacetate, polyethylene glycol di(3-mercaptopropionate), trimethylolethane tri(3-mercaptopropionate), trimethylolethane trithioglycolate, trimethylolpropane tri(3-mercaptopropionate), trimethylolpropane trithioglycolate, dithioethane, di- or trithiopropane and 1,6-hexane dithiol. The crosslinking promoter is added to the uncrosslinked hydrophilic polymer to promote covalent crosslinking thereof, or to a blend of the uncrosslinked hydrophilic polymer and the complementary oligomer, to provide crosslinking between the two components.

The hydrophilic polymer may also be crosslinked prior to admixture with the complementary oligomer. In such a case, it may be preferred to synthesize the polymer in crosslinked form, by admixing a monomeric precursor to the polymer with multifunctional comonomer and copolymerizing. Examples of monomeric precursors and corresponding polymeric products are as follows: N-vinyl amide precursors for a poly(N-vinyl amide) product; N-alkylacrylamides for a poly(N-alkylacrylamide) product; acrylic acid for a polyacrylic acid product; methacrylic acid for a polymethacrylic acid product; acrylonitrile for a poly(acrylonitrile) product; and N-vinyl pyrrolidone (NVP) for a poly(vinylpyrrolidone) (PVP) product. Polymerization may be carried out in bulk, in suspension, in solution, or in an emulsion. Solution polymerization is preferred, and polar organic solvents such as ethyl acetate and lower alkanols (e.g., ethanol, isopropyl alcohol, etc.) are particularly preferred. For preparation of hydrophilic vinyl polymers, synthesis will typically take place via a free radical polymerization process in the presence of a free radical initiator as described above. The multifunctional comonomer include, for example, bisacrylamide, acrylic or methacrylic esters of diols such as butanediol and hexanediol (1,6-hexane diol diacrylate is preferred), other acrylates such as pentaerythritol tetraacrylate, and 1,2-ethylene glycol diacrylate, and 1,12-dodecanediol diacrylate. Other useful multifunctional crosslinking monomers include oligomeric and polymeric multifunctional (meth) acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as EBECRYL® 270 and EBECRYL® 230 (1500 weight average molecular weight and 5000 weight average molecular weight acrylated urethanes, respectively—both available from UCB of Smyrna, Ga.), and combinations thereof. If a chemical crosslinking agent is employed, the amount used will preferably be such that the weight ratio of crosslinking agent to hydrophilic polymer is in the range of about 1:100 to 1:5. To achieve a higher crosslink density, if desired, chemical crosslinking is combined with radiation curing.

The compositions are self-adhesive and normally do not require the addition of tackifiers. However, tackifiers may, if desired, be included. Suitable tackifiers are relatively low molecular weight resins (weight average molecular weight generally less than about 50,000) having a fairly high glass transition temperature. Tackifying resins include, for example, rosin derivatives, terpene resins, and synthetic or naturally derived petroleum resins. If tackifiers are incorporated into the present compositions, preferred tackifying resins are generally selected from the group of non-polar tackifying resins, such as Regalrez® 1085 (a hydrogenated hydrocarbon resin) and Regalite® Resins such as Regalite® 1900, available from Hercules, Escorez 1304 (also a hydrocarbon resins) and Escorez® 1102 available from Exxon Chemical Company, Wingtac® 95 (a synthetic polyterpene resin), or Wingtack® 85, available from Goodyear Tire and Rubber. The resin represents approximately 5 wt. % to about 15 wt. %, preferably 7.5 wt. % to 12 wt. %, and preferably 7.5 wt. % to 10 wt. %, relative to the dry adhesive composition.

Other components that can be advantageously incorporated into the adhesive compositions of the invention are, like the hydrophilic polymer/complementary oligomer blend, water-absorbent materials. Such components include cellulosic polymers, e.g., cellulose esters and analogs, with sodium carboxymethylcellulose (CMC) and hydroxypropyl cellulose preferred, and with sodium CMC most preferred. Naturally hydrophilic sorbents may also be used, e.g., collagens and glycosaminoglycans.

Incorporation of an antioxidant is optional but preferred. The antioxidant serves to enhance the oxidative stability of the composition. Heat, light, impurities, and other factors can all result in oxidation of the composition. Thus, ideally, antioxidants should protect against light-induced oxidation, chemically induced oxidation, and thermally induced oxidative degradation during processing and/or storage. Oxidative degradation, as will be appreciated by those in the art, involves generation of peroxy radicals, which in turn react with organic materials to form hydroperoxides. Primary antioxidants are peroxy free radical scavengers, while secondary antioxidants induce decomposition of hydroperoxides, and thus protect a material from degradation by hydroperoxides. Most primary antioxidants are sterically hindered phenols, and preferred such compounds for use herein are tetrakis [methylene (3,5-di-tert-butyl-4-hydroxy-hydrocinnamate)] methane (e.g., Irganox® 1010, from Ciba-Geigy Corp., Hawthorne, N.Y.) and 1,3,5-trimethyl-2,4,6-tris[3,5-di-t-butyl-4-hydroxy-benzyl]benzene (e.g., Ethanox® 330, from Ethyl Corp.). A particularly preferred secondary antioxidant that may replace or supplement a primary antioxidant is tris(2,4-di-tert-butylphenyl)phosphite (e.g., Irgafos® 168, Ciba-Geigy Corp.). Other antioxidants, including but not limited to multi-functional antioxidants, are also useful herein. Multifunctional antioxidants serve as both a primary and a secondary antioxidant. Irganox® 1520 D, manufactured by Ciba-Geigy is one example of a multifunctional antioxidant. Vitamin E antioxidants, such as that sold by Ciba-Geigy as Irganox® E17, are also useful in the present adhesive compositions. Other suitable antioxidants include, without limitation, ascorbic acid, ascorbic palmitate, tocopherol acetate, propyl gallate, butylhydroxyanisole (BHA), butylated hydroxytoluene (BHT), bis(1,2,2,6,6-pentamethyl-4-piperidinyl)-(3,5-di-tert-butyl-4-hydroxybenzyl)butylpropanedioate, (available as Tinuvin®144 from Ciba-Geigy Corp.) or a combination of octadecyl 3,5-di-tert-butyl-4-hydroxyhydrocinnamate (also known as octadecyl 3-(3',5'-di-tert-butyl-4'-hydroxyphenyl)-propionate) (available as Naugard® 76 from Uniroyal Chemical Co., Middlebury, Conn.) and bis(1,2,2,6,6-pentamethyl-4-piperidinyl sebacate) (available as Tinuvin®765 from Ciba-Geigy Corp.). Preferably, the antioxidant is present in amount up to about 2 wt. % of the adhesive composition; typically, the amount of antioxidant is in the range of about 0.05 wt. % to 1.5 wt. %.

However, other additives may be incorporated into the present adhesive compositions, so long as they are not detrimental to the composition in any way. The adhesive composition may also include conventional additives such as fillers, chain transfer agents for controlling molecular weight (e.g., carbon tetrabromide, mercaptans, or alcohols), preservatives, pH regulators, softeners, thickeners, pigments, dyes, refractive particles, stabilizers, toughening agents, pharmaceutical agents, and permeation enhancers.

Absorbent fillers may be advantageously incorporated to control the degree of hydration when the adhesive is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Cab-O-Sil® (Cabot Corporation, Boston Mass.).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, or citric acid-phosphate buffers may also be included so as to ensure that the pH of the adhesive composition is compatible with that of an individual's body surface.

Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

Preferred thickeners herein are naturally occurring compounds or derivatives thereof, and include, by way of example: collagen; galactomannans; starches; starch derivatives and hydrolysates; cellulose derivatives such as methylcellulose, hydroxypropylcellulose, hydroxyethyl cellulose, and hydroxypropyl methylcellulose; colloidal silicic acids; and sugars such as lactose, saccharose, fructose, and glucose. Synthetic thickeners such as polyvinyl alcohol, vinylpyrrolidone-vinylacetate-copolymers, polyethylene glycols, and polypropylene glycols may also be used.

Low molecular weight plasticizers may also be incorporated into the composition, including, without limitation, the following: dialkyl phthalates, dicycloalkyl phthalates, diaryl phthalates and mixed alkyl-aryl phthalates as represented by dimethyl phthalate, diethyl phthalate, dipropyl phthalate, di(2-ethylhexyl)phthalate, di-isopropyl phthalate, diamyl phthalate and dicapryl phthalate; alkyl and aryl phosphates such as tributyl phosphate, trioctyl phosphate, tricresyl phosphate, and triphenyl phosphate; alkyl citrate and citrate esters such as trimethyl citrate, triethyl citrate, tributyl citrate, acetyl triethyl citrate, and trihexyl citrate; alkyl adipates such as dioctyl adipate, diethyl adipate, di(2-methylethyl)adipate, and dihexyl adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; and low molecular weight polyalkylene glycols (molecular weight 300 to 600) such as polyethylene glycol 400; and mixtures thereof.

III. Adhesive Compositions Containing an Active Agent:

Any of the above-described adhesive compositions may be modified so as to contain an active agent and thereby act as an active agent delivery system when applied to a body surface in active agent-transmitting relation thereto. The release of active agents "loaded" into the present compositions typically involves both absorption of water and desorption of the agent via a swelling-controlled diffusion mechanism. Active agent-containing adhesive compositions may be employed, by way of example, in transdermal drug delivery systems, in wound dressings, in topical pharmaceutical formulations, in implanted drug delivery systems, in oral dosage forms, and the like.

Suitable active agents that may be incorporated into the present compositions and delivered systemically (e.g., with a transdermal, oral, or other dosage form suitable for systemic administration of a drug) include, but are not limited to: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, antianginal agents, central nervous system (CNS) agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, nitroglycerine, verapamil, propranolol, silabolin, foridone, clonidine, cytisine, phenazepam, nifedipine, fluacizin, and salbutamol.

For topical drug administration and/or medicated cushions (e.g., medicated footpads), suitable active agents include, by way of example, the following:

Bacteriostatic and bactericidal agents: Suitable bacteriostatic and bactericidal agents include, by way of example: halogen compounds such as iodine, iodopovidone complexes (i.e., complexes of PVP and iodine, also referred to as "povidine" and available under the tradename Betadine® from Purdue Frederick), iodide salts, chloramine, chlorohexidine, and sodium hypochlorite; silver and silver-containing compounds such as sulfadiazine, silver protein acetyltannate, silver nitrate, silver acetate, silver lactate, silver sulfate and silver chloride; organotin compounds such as tri-n-butyltin benzoate; zinc and zinc salts; oxidants, such as hydrogen peroxide and potassium permanganate; aryl mercury compounds, such as phenylmercury borate or merbromin; alkyl mercury compounds, such as thiomersal; phenols, such as thymol, o-phenyl phenol, 2-benzyl-4-chlorophenol, hexachlorophen and hexylresorcinol; and organic nitrogen compounds such as 8-hydroxyquinoline, chlorquinaldol, clioquinol, ethacridine, hexetidine, chlorhexedine, and ambazone.

Antibiotic agents: Suitable antibiotic agents include, but are not limited to, antibiotics of the lincomycin family (referring to a class of antibiotic agents originally recovered from streptomyces lincolnensis), antibiotics of the tetracycline family (referring to a class of antibiotic agents originally recovered from streptomyces aureofaciens), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl]amino]-1-thio-L-threo-α-D-galactooctopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]-amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself 4-(dimethylamino)-1,4,4α,5,5α,6,11,12α-octahydro-3,6,12,12α-pentahydroxy-6-methyl-1,11-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Pain relieving agents: Suitable pain relieving agents are local anesthetics, including, but not limited to, acetamidoeugenol, alfadolone acetate, alfaxalone, amucaine, amolanone, amylocaine, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocaine are referred pain relieving agents herein.

Other topical agents that may be delivered using the present compositions as drug delivery systems include the following: antifungal agents such as undecylenic acid, tolnaftate, miconazole, griseofulvine, ketoconazole, ciclopirox, clotrimazole and chloroxylenol; keratolytic agents, such as salicylic acid, lactic acid and urea; vessicants such as cantharidin; anti-acne agents such as organic peroxides (e.g., benzoyl peroxide), retinoids (e.g., retinoic acid, adapalene, and tazarotene), sulfonamides (e.g., sodium sulfacetamide), resorcinol, corticosteroids (e.g., triamcinolone), alpha-hydroxy acids (e.g., lactic acid and glycolic acid), alpha-keto acids (e.g., glyoxylic acid), and antibacterial agents specifically indicated for the treatment of acne, including azelaic acid, clindamycin, erythromycin, meclocycline, minocycline, nadifloxacin, cephalexin, doxycycline, and ofloxacin; skin-lightening and bleaching agents, such as hydroquinone, kojic acid, glycolic acid and other alpha-hydroxy acids, artocarpin, and certain organic peroxides; agents for treating warts, including salicylic acid, imiquimod, dinitrochlorobenzene, dibutyl squaric acid, podophyllin, podophyllotoxin, cantharidin, trichloroacetic acid, bleomycin, cidofovir, adefovir, and analogs thereof; and anti-inflammatory agents such as corticosteroids and nonsteroidal anti-inflammatory drugs (NSAIDs), where the NSAIDS include ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, and tiaprofenic acid.

For wound dressings, suitable active agents are those useful for the treatment of wounds, and include, but are not limited to bacteriostatic and bactericidal compounds, antibiotic agents, pain relieving agents, vasodilators, tissue-healing enhancing agents, amino acids, proteins, proteolytic enzymes, cytokines, and polypeptide growth factors. Specific such agents are set forth in Section IX, infra.

For topical and transdermal administration of some active agents, and in wound dressings, it may be necessary or desirable to incorporate a permeation enhancer into the composition in order to enhance the rate of penetration of the agent into or through the skin. Suitable enhancers include, for example, the following: sulfoxides such as dimethylsulfoxide (DMSO) and decylmethylsulfoxide ($C_{10}$MSO); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclaza-cycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

IV. Conductive Adhesive Compositions:

The compositions of the invention can be rendered electrically conductive for use in biomedical electrodes and other electrotherapy contexts, i.e., to attach an electrode or other electrically conductive member to the body surface. For example, the adhesive composition may be used to attach a transcutaneous nerve stimulation electrode, an electrosurgical return electrode, or an EKG electrode to a patient's skin or mucosal tissue. These applications involve modification of the composition so as to contain a conductive species. Suitable conductive species are ionically conductive electrolytes, particularly those that are normally used in the manufacture of conductive adhesives used for application to the skin or other body surface, and include ionizable inorganic salts, organic compounds, or combinations of both. Examples of ionically conductive electrolytes include, but are not limited to, ammonium sulfate, ammonium acetate, monoethanolamine acetate, diethanolamine acetate, sodium lactate, sodium citrate, magnesium acetate, magnesium sulfate, sodium acetate, calcium chloride, magnesium chloride, calcium sulfate, lithium chloride, lithium perchlorate, sodium citrate and potassium chloride, and redox couples such as a mixture of ferric and ferrous salts such as sulfates and gluconates. Preferred salts are potassium chloride, sodium chloride, magnesium sulfate, and magnesium acetate, and potassium chloride is most preferred for EKG applications. Although virtually any amount of electrolyte may be present in the adhesive compositions of the invention, it is preferable that any electrolyte present be at a concentration in the range of about 0.1 to about 15 wt. % of the adhesive composition. The procedure described in U.S. Pat. No. 5,846,558 to Nielsen et al. for fabricating biomedical electrodes may be adapted for use with the adhesive compositions of the invention, and the disclosure of that patent is incorporated by reference with respect to manufacturing details. Other suitable fabrication procedures may be used as well, as will be appreciated by those skilled in the art.

Any absorbent additives incorporated should be compatible with all components of the hydrogel-containing cushion, and should also serve to reduce or eliminate cold flow under compression. Suitable absorbent additives include, by way of example, polyacrylate starch derivatives, starches, starch copolymers, and the like.

V. Fabrication Processes:

The compositions of the invention are generally prepared by separately incorporating the necessary curing agents into each phase, and then blending the phases. That is, the curing agent for the hydrophobic phase, along with any catalysts or co-curing agents, are loaded into the composition that will serve as the hydrophobic phase, and, if applicable, the curing agent for the hydrophilic phase is loaded into the composition that will serve as the hydrophilic phase. At this point, the hydrophobic and hydrophilic compositions are mixed and curing is conducted using the appropriate means, e.g., radiation or heat.

VI. Wound Dressings:

In a further embodiment, the compositions of the invention are as absorbent materials in a wound dressing. The composition may be formulated so as to contain a pharmacologically active agent. Preferred active agents, in this embodiment, include the bacteriostatic and bactericidal agents, antibiotic agents, and pain-relieving agents set forth in Section IV, as well as the following:

Topical Vasodilators: Such compounds are useful for increasing blood flow in the dermis, and preferred topical vasodilators are those known as rubefacients or counterirritants. Rubefacient agents include nicotinic acid, nicotinates such as methyl, ethyl, butoxyethyl, phenethyl and thurfyl nicotinate, as well as the essential oils such as mustard, turpentine, cajuput and capsicum oil, and components thereof. Particular preferred such compounds include, but are not limited to, methyl nicotinate, nicotinic acid, nonivamide, and capsaicin.

Proteolytic enzymes: Proteolytic enzymes herein are those that are effective wound cleansing agents, and include, for example, pepsin, trypsin, collagenase, chymotrypsin, elastase, carboxypeptidase, aminopeptidase, and the like.

Peptide, proteins, and amino acids: Suitable peptides and proteins are tissue-healing enhancing agents (also referred to in the art as "tissue regenerative agents") such as collagen, glycosaminoglycans (e.g., hyaluronic acid, heparin, heparin sulfate, chondroitin sulfate, etc.), proteoglycans (e.g., versican, biglycan) substrate adhesion molecules (e.g., fibronectin, vitronectin, laminin), polypeptide growth factors (e.g., platelet-derived growth factor, a fibroblast growth factor, a transforming growth factor, an insulin-like growth factor, etc.), and other peptides such as fibronectin, vitronectin, osteopontin, and thrombospondin, all of which contain the tripeptide sequence RGD (arginine-glycine-aspartic acid), a sequence generally associated with adhesive proteins and necessary for interaction with cell surface receptors.

One embodiment of a wound dressing of the invention is represented in FIG. 1. The wound dressing is generally indicated at 10, and comprises: an outer backing layer 12 that serves as the external surface of the dressing following application to the body surface; a skin contact adhesive layer 14 laminated thereto, which may or may not be an adhesive composition of the invention, optionally containing one or more pharmacologically active agents; an absorbent wound-contacting region 16 comprised of an adhesive composition of the invention and located on the on the wound contacting side of layer 14; and a removable release liner 18. Upon removable of the release liner, the dressing is applied to a body surface in the region of a wound, and placed on the body surface so that the wound-contacting region 16 is directly over the wound. In this embodiment, the wound dressing adheres to the skin surrounding the wound as a result of the exposed skin contact adhesive areas 20 and 22 surrounding the wound-contacting region. If the wound-contacting composition is prepared so that it has some degree of tack prior to absorption of water (as in, e.g., wound exudate), the dressing adheres in the central region as well. It should be noted that any of the adhesive compositions of the invention may be used as a wound dressing herein, providing that, as noted above, the adhesive composition is substantially nontacky or at most slightly tacky. Also, those adhesive compositions that exhibit a high degree of absorbency are preferred. The other components of the wound dressing of FIG. 1 are as follows:

The backing layer 12 of the wound dressing functions as the primary structural element and provides the dressing with flexibility. The material used for the backing layer should be inert and incapable of absorbing drug, enhancer or other components of the wound-contacting adhesive composition. Also, the material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing. The layer is preferably although not necessarily nonocclusive (or "breathable"), i.e., is preferably permeable to moisture.

The skin contact adhesive layer 14 may be composed of a conventional pressure-sensitive adhesive such as may be selected from polysiloxanes, polyisobutylenes, polyacrylates, polyurethanes, polyisobutylene, and the like. Alternatively, the layer may be made from an adhesive composition of the invention, as described in Sections II, III and IV, supra.

Release liner 18 is a disposable element that serves to protect the device prior to application. The release liner should be formed from a material impermeable to the drug, vehicle and adhesive, and that is easily stripped from the contact adhesive. Release liners are typically treated with silicone or fluorocarbons, and are commonly made from polyesters and polyethylene terephthalate.

Figure 2:
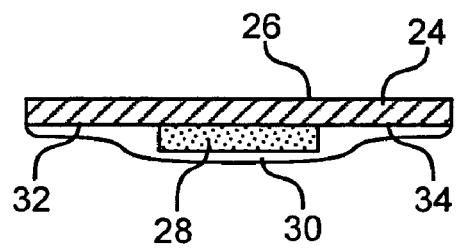
FIG. 2 schematically illustrates an alternative embodiment of a wound dressing of the invention that does not include separate backing and skin contact adhesive layers, wherein a backing layer is composed of a skin contact adhesive having a nontacky outwardly facing surface and a slightly tacky body facing surface, and an adhesive composition of the invention is present as a film on an interior region of the body-contacting, at least slightly tacky surface of the backing layer.

In another embodiment, illustrated in FIG. 2, the backing layer 24 of the wound dressing shown is composed of a tacky or at least slightly tacky adhesive composition of the invention, but is provided with a nontacky upper surface 26. The wound-contacting hydrogel material 28 is adhered to the skin-contacting side of the backing layer 24. Upon removal of release liner 30, the wound dressing is applied to an individual's skin in the region of a wound so that the wound-contacting hydrogel material is placed directly over the wound. As with the embodiment of FIG. 1, the wound dressing adheres to the body surface by virtue of the exposed regions 32 and 34 of the adhesive composition. In this case, it is preferred that both the backing layer and the adhesive composition be translucent, so that the extent of wound healing can be viewed directly through the backing, eliminating the need for frequent replacement or removal of the wound dressing.

Figure 3:
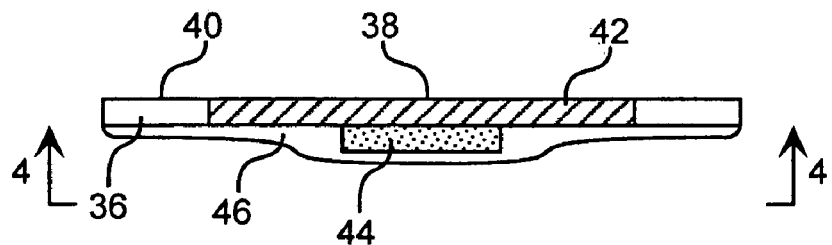
FIG. 3 schematically illustrates another embodiment of a wound dressing of the invention, wherein the dressing is similar in structure to that of FIG. 2, but includes a peripheral skin contact adhesive on the body-contacting surface. In this case, the body-contacting surface of the backing layer does not need to be tacky.

In a further embodiment, illustrated in FIG. 3, the perimeter 36 of the wound dressing is made of a different material than the interior region 38 of the backing. In this case, the perimeter 36 is comprised of a skin contact adhesive that may or may not be an adhesive composition of the invention, although the upper, outwardly facing surface 40 of the perimeter is nontacky. The interior region 38 of the backing is preferably comprised of an adhesive composition of the invention. The skin-facing side of the interior region 38 may or may not be tacky, although the upper surface 42 of the interior region 38 should be nontacky. The wound-contacting hydrogel material 44 is adhered to the underside (i.e., the skin contacting side) of the backing and is centrally located within interior region 38. As with the embodiment of FIG. 2, it is preferred that both the interior region 38 of the backing and the wound-contacting hydrogel material 44 are translucent. Generally, the perimeter adhesive will be opaque. The removable release liner is indicated at 46. In a variation on the embodiment of FIG. 3, an outer layer may be laminated to the upper surface of the device shown. Such an outer layer would then serve as the actual backing, with the layer represented by interior region 38 and perimeter 36 representing an intermediate layer.

Figure 4:
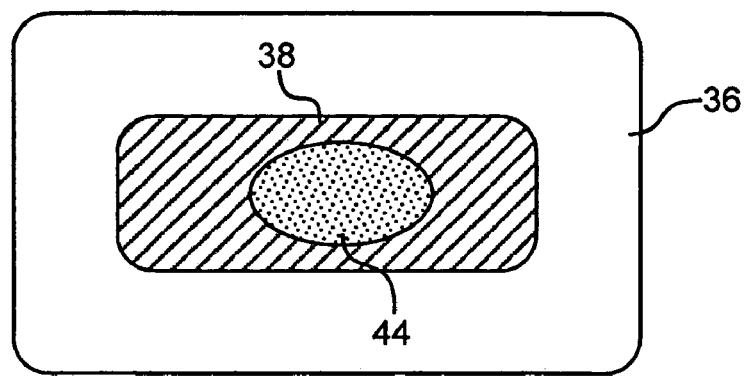
FIG. 4 is a bottom plan view of the embodiment of FIG. 3 taken along the 4—4 lines of that figure, and illustrates the concentric regions of the body-contacting surface, with a peripheral skin contact adhesive surrounding an inner region of a nontacky or slightly tacky material, which in turn contains the adhesive composition in a central region intended as the wound-contacting region.

FIG. 4 is a bottom plan view of the wound dressing of FIG. 3 (with the release liner having been removed), taken along lines 4—4; the view shown is thus the skin-contacting face of the dressing. As described with respect to FIG. 3, the wound-contacting hydrogel material 44 is located within the interior region 38 of the backing, and the perimeter adhesive 36 surrounds that region.

Figure 5:
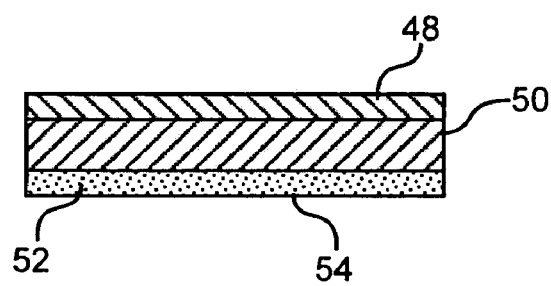
FIG. 5 illustrates another embodiment of a wound dressing herein wherein the three layers of a laminated composite, an outwardly facing backing layer, an interior pressure sensitive adhesive layer, and a body-contacting layer composed of an adhesive composition of the invention, are coextensive.

In still another embodiment, illustrated in FIG. 5, the wound dressing contains three layers, a backing layer 48, a central adhesive layer 50 typically composed of a conventional pressure-sensitive adhesive, and a wound-contacting hydrogel layer 52, wherein the three layers are coextensive such that there is no distinct perimeter region as there is in the embodiments of FIG. 1 to 4. During storage and prior to use, the skin contacting side 54 of the dressing is protected with a release liner (not shown), as above.

Figure 6:
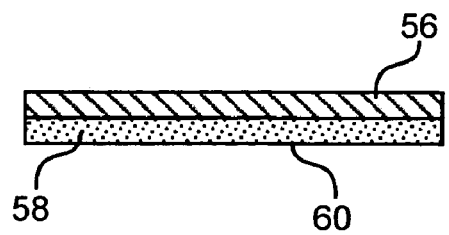
FIG. 6 illustrates an analogous embodiment wherein the interior pressure sensitive adhesive layer is omitted, and the hydrogel-containing layer is made sufficiently tacky so that the backing layer adheres directly thereto. Again, the backing layer and the body-contacting hydrogel layer are coextensive.

FIG. 6 illustrates a variation of the embodiment of FIG. 5, wherein the wound dressing is composed of only two layers, a backing 56 and a wound-contacting hydrogel layer 58 laminated thereto and coextensive therewith. In this case, the hydrogel layer 58 must have sufficient tack so as to adhere to the backing layer, even after water absorption. As with the embodiments discussed above, the skin contacting side 60 is protected with a release liner (not shown) during storage and prior to use.

VII. Active Agent Delivery Systems:

An active agent may be delivered to a body surface by simply placing a composition of the invention on a body surface in active agent-transmitting relation thereto. Alternatively, an active agent-containing composition may be incorporated into a delivery system or "patch." In manufacturing such systems, the hydrogel adhesive composition may be cast or extruded onto a backing layer or release liner and will serve as the skin-contacting face of the system and act as an active agent reservoir. Alternatively, the adhesive composition may be used as an active agent reservoir within the interior of such a system, with a conventional skin contact adhesive laminated thereto to affix the system to a patient's body surface.

Systems for the topical, transdermal or transmucosal administration of an active agent may comprise: (A) a reservoir containing a therapeutically effective amount of an active agent; (B) an adhesive means for maintaining the system in active agent transmitting relationship to a body surface; and (C) a backing layer as described in the preceding section, wherein (D) a disposable release liner covers the otherwise exposed adhesive, protecting the adhesive surface during storage and prior to use (also as described in the preceding section). In many such devices, the reservoir can also serve as the adhesive means, and the adhesive compositions of the invention can be used as the reservoir and/or the adhesive means.

Any number of active agents can be administered using such delivery systems. Suitable active agents include the broad classes of compounds normally delivered to and/or through body surfaces and membranes; such active agents are described in Section V. With some active agents, it may be necessary to administer the agent along with a permeation enhancer in order to achieve a therapeutically effective flux through the skin. Suitable enhancers are also described in Section IV.

Accordingly, an active agent-containing composition is incorporated into the reservoir, either during manufacture of the system or thereafter. The composition will contain a quantity of an active agent effective to provide the desired dosage over a predetermined delivery period. The composition will also contain a carrier (e.g., a vehicle to solubilize the active agent), a permeation enhancer, if necessary, and optional excipients such as colorants, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Preferably, the delivery system is "monolithic," meaning that a single layer serves as both the active agent-containing reservoir and the skin contact adhesive. However, the reservoir and the skin contact adhesive may be separate and distinct layers. Also, more than one reservoir may be present, each containing a different component for delivery into the skin. The present adhesive compositions may be used as any or all of the aforementioned layers.

The backing layer of the drug delivery system functions as the primary structural element of the transdermal system, and preferred backing materials in transdermal drug delivery devices are the same as those described in the preceding section with respect to wound dressings.

Additional layers, e.g., intermediate fabric layers and/or rate-controlling membranes, may also be present in a transdermal drug delivery system. Fabric layers may be used to facilitate fabrication of the device, while a rate-controlling membrane may be used to control the rate at which a component permeates out of the device. The component may be a drug, a permeation enhancer, or some other component contained in the drug delivery system.

In any of these systems, it may be desirable to include a rate-controlling membrane in the system on the body surface side of the drug reservoir. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

The compositions of the invention may also serve to deliver an active agent using other routes of administration. For example, the compositions may be formulated with excipients, carriers and the like suitable for oral administration of an orally active drug. The compositions may also be used in buccal and sublingual drug delivery, insofar as the compositions can adhere well to moist surfaces within the mouth. In buccal and sublingual systems, hydrolyzable and/or bioerodible polymers may be incorporated into the compositions to facilitate gradual erosion throughout a drug delivery period. Still other types of formulations and drug delivery platforms may be prepared using the present compositions, including implants, rectally administrable compositions, vaginally administrable compositions, and the like.

IX. Cushions and Other Products Requiring Adhesion to a Body Surface:

The adhesive compositions of the invention are useful in any number of additional contexts wherein adhesion of a product to a body surface is called for or desirable. These applications include, for example, pressure-relieving cushions for application to a foot, wherein the cushions may or may not contain medication for transdermal or topical delivery, e.g., in the treatment of dicubitis, veinous and diabetic foot ulcers, or the like. Suitable active agents are described in Section IV.

Such cushions will generally be comprised of a flexible, resilient outer layer, fabricated from a foam pad or fabric, with a layer of an adhesive composition of the invention laminated thereto for application to the skin surface. Suitable cushions include heel cushions, elbow pads, knee pads, shin pads, forearm pads, wrist pads, finger pads, corn pads, callus pads, blister pads, bunion pads and toe pads.

The compositions of the invention are also useful in a host of other contexts, e.g., as adhesives for affixing medical devices, diagnostic systems and other devices to be affixed to a body surface, and in any other application wherein adhesion to a body surface is necessary or desired. The adhesive compositions are also useful as sealants for ostomy devices, prostheses, and face masks, as sound, vibration or impact absorbing materials, as carriers in cosmetic and cosmeceutical gel products, and will have other uses known to or ascertainable by those of ordinary skill in the art, or as yet undiscovered.

The practice of the present invention will employ, unless otherwise indicated, conventional techniques of polymer chemistry, adhesive manufacture, and hydrogel preparation, which are within the skill of the art. Such techniques are fully explained in the literature.

It is to be understood that while the invention has been described in conjunction with the preferred specific embodiments thereof, the foregoing description, as well as the examples that follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

The following abbreviations and tradenames are used in the examples:

Br-APFR (SP-1055): dibromo-terminated alkyl phenolformaldehyde resin (Schenectady)
APFR: alkyl phenolformaldehyde resin (identical to SP-1055 but containing terminol methylol groups) (obtained from M.V. Lomonosov Moscow State Academy of Fine Chemical Technology)
BPO: benzoyl peroxide
BR: butyl rubber, 2 wt. % isoprene content
HPC: hydroxypropyl cellulose
PIB: polyisobutylene
RH: relative humidity
SR 399: dipentaerythritol monohydroxypentaacrylate (Sartomer)

EXAMPLE 1

The following example describe formulation of a pressure-sensitive adhesive composition based on a cured blend of polyisobutylene with butyl rubber with PVP-PEG water sorbents, and optionally with cellulose-based water sorbents, to form a two-phase adhesive matrix.

Mixing procedures for the adhesive blend: Two methods of mixing were used: a laboratory mixer of rotor-plunger type (I) and a Haake mixer supplied with a sigma-blade and Banbary rotors (II). With the latter method, a sample is loaded into a working chamber and heated to the desired temperature, at which point a rotating agitator was introduced to a predetermined depth to mix the composition. This procedure was repeated several times to obtain a homogeneous mixture. The temperature-time regime of mixing depended on the components used, particularly on the curing agent used. Usually, mixing may be carried out at a temperature >100° C. However, if Br-APFR was used as the curing agent, the temperature was decreased to 60° C. and the curing agent then added to the PIB-BR blend. The temperature profile was similar when a Haake mixer was used. The homogeneity of mixing was established by achieving of a stable level of a torque and confirmed microscopically by analyzing a pressed adhesive film.

Pressing and curing adhesive films: The prepared adhesive blends were pressed between two release liners at an applied pressure in the range of 1 to 3 MPa. The formulations loaded with APFR curing agent were hot-pressed at 120° C., whereas the formulations loaded with SP1055 curing agent and mixed in the Haake were pressed at room temperature. The adhesive films loaded with APFR were then cured by annealing in an oven at 160° C. for one hour. The adhesive films loaded with SP1055 were cured at 120° C. for 30 minutes.

Patch preparation: The cured adhesive films were laminated to PU backing film with subsequent die cutting of the patches. The thickness of the adhesive layer in the obtained patches varied from 350 to 700 μm. To provide a gradual decrease of adhesive layer thickness toward patch edges, pressing molds were designed and constructed with the thickness of central part ~500–700 μm and peripheral part of 100–200 μm.

Figure 7:
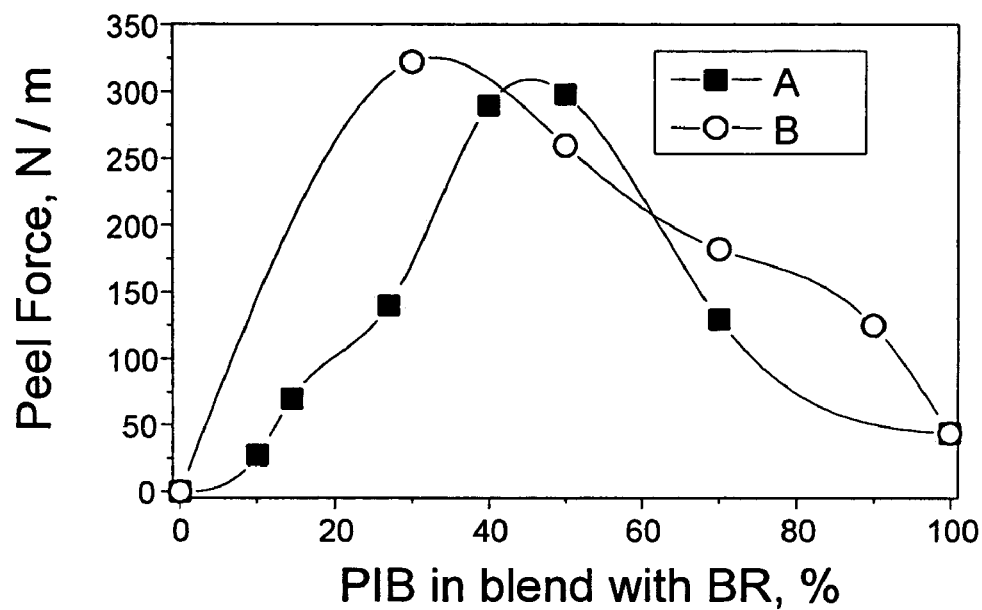
FIG. 7 shows the peel strength of PIB-BR blends pressed between a polyethylene substrate.

Preparation of the hydrophobic phase: The hydrophobic phase was prepared by blending PIB with BR. Although neither PIB nor BR is a good adhesive, mixing the two results in enhancement of adhesive properties within a wide concentration range, as indicated in FIG. 7. That figure gives the peel strength data obtained for a PIB/BR blends at a range of PIB:BR ratios. As the maximum peel strength was observed with a blend containing 40% of PIB and 60% BR, that composition was used as a basis for preparation of an adhesive composition according to the invention. In FIG. 7, Curve A was produced by tenfold PIB-BR film pressing at a compression stress of 1–2 MPa and a temperature of 120° C., while Curve B was produced by mixing with a high speed mixer at a temperature of 170° C. for 20 minutes prior to curing the adhesive film. To obtain cohesive strength (e.g., for cushions and other pressure-relieving or weight-bearing applications), the PIB-BR blend should be cured. Since PIB contains no double bonds and cannot be crosslinked, curing g the PIB-BR blends is made possible via BR crosslinking.

EXAMPLE 2

Figure 8:
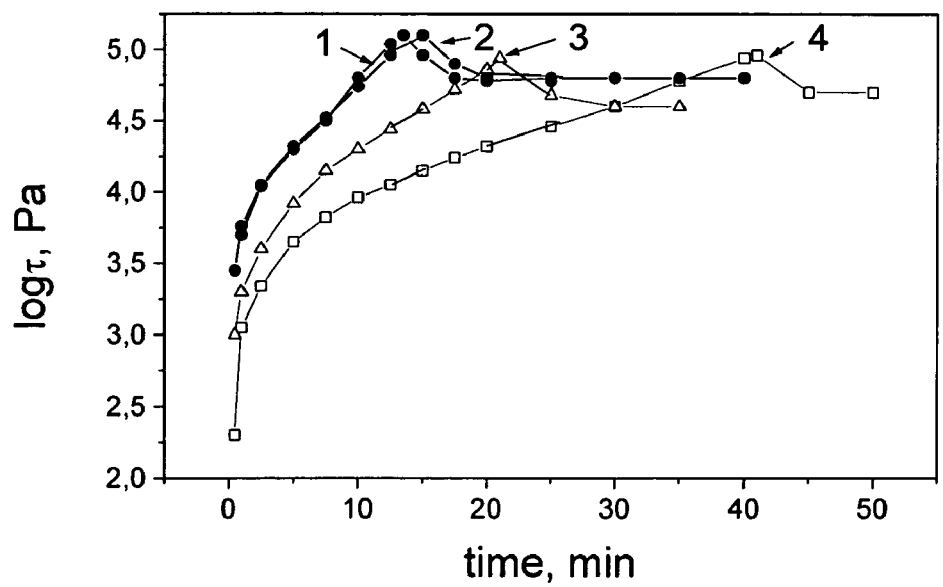
FIG. 8 shows the effect of curing agent concentration and temperature on the rheokinetics of PVP-PEG hydrogel thermal crosslinking, as described in Example 2.

Curing a PVP-PEG hydrogel dispersed within the hydrophobic polymer:

Cured PVP-PEG hydrogels were found to be highly hygroscopic. At relatively low degrees of hydration, these hydrogels provide adhesive and viscoelastic properties that allow them to be used for SCA matrices in cushion patches. If, however, such hydrogels absorb more than about 15% water, they swell so much that they become unsuitable for cushion usage. In order to decrease the PVP-PEG hydrogel hygroscopicity, it was found useful to mix the hydrogel with an appropriate hydrophobic adhesive. The following experimental work was carried out to determine conditions under which such mixtures can be cured so that they become viscoelastic at room temperature and have adhesive properties suitable for use in cushion pads. In these experiments, a PVP-PEG hydrogel was mixed with a PIB-BR-Regalite adhesive. UV-curing to produce PVP-PEG crosslinking, employing dipentaerythritol monohydroxy pentaacrylate SR 399 (Sartomer) as curing agent and benzoyl peroxide (BPO) as an initiator of radical polymerization, was implemented at elevated temperatures. The results of these experiments are shown in FIG. 8. In FIG. 8, the indivudal curves are as follows—1: SR/PVP weight ratio is 5, T=100° C. 2: SR/PVP=5, 90° C. 3: SR/PVP=2, 105° C. 4: SR/PVP=2, 95° C. As can be seen in this figure, crosslinking was found to start at about 80° C. At relatively high SR 399 loading, the curing took about 15 min, both at 90 and 100° C. At lower curing agent concentrations, the crosslinking took longer, whereas an increase in temperature accelerated the curing significantly. The maximum achieved level of shear stress, which relates to the blend viscosity and crosslinking density, was found to be nearly independent of the SR 399/PVP ratio.

Figure 9:
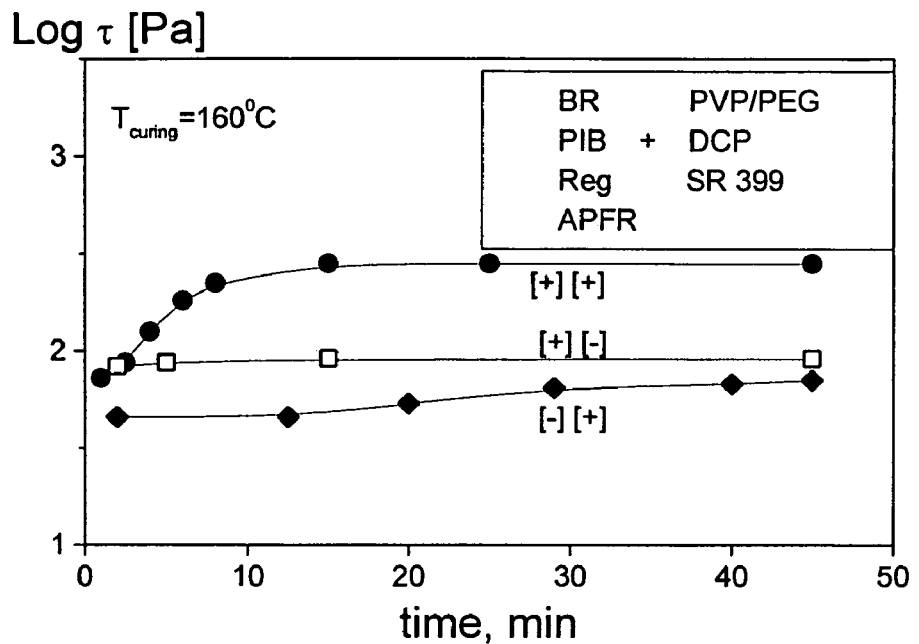
FIG. 9 illustrates the curing rheokinetics of PIB-BR-Regalite mixtures with an incorporated PVP-PEG hydrogel, as described in Example 2.

Next, experiments were performed in which the PVP-PEG hydrogel, with or without curing agent SR 399, was mixed with PIB-BR-Regalite hydrophobic adhesive, with or without APFR as a curing (crosslinking) agent. The mixtures were cured at 160° C. As shown in FIG. 9, curing only occurred if both phases (hydrophobic and hydrophilic) contained their relevant crosslinkers. In FIG. 9, the first [+] or [−] sign refers to the presence or absence of curing agent in the hydrophobic phase, while the second [+] or [−] sign refers to the presence or absence of curing agent in the hydrophilic phase. In order for the mixture to cure and blend properly, each phase (hydrophobic and hydrophilic) had to be loaded with its relevant crosslinker prior to mixing.

EXAMPLE 3

Figure 10:
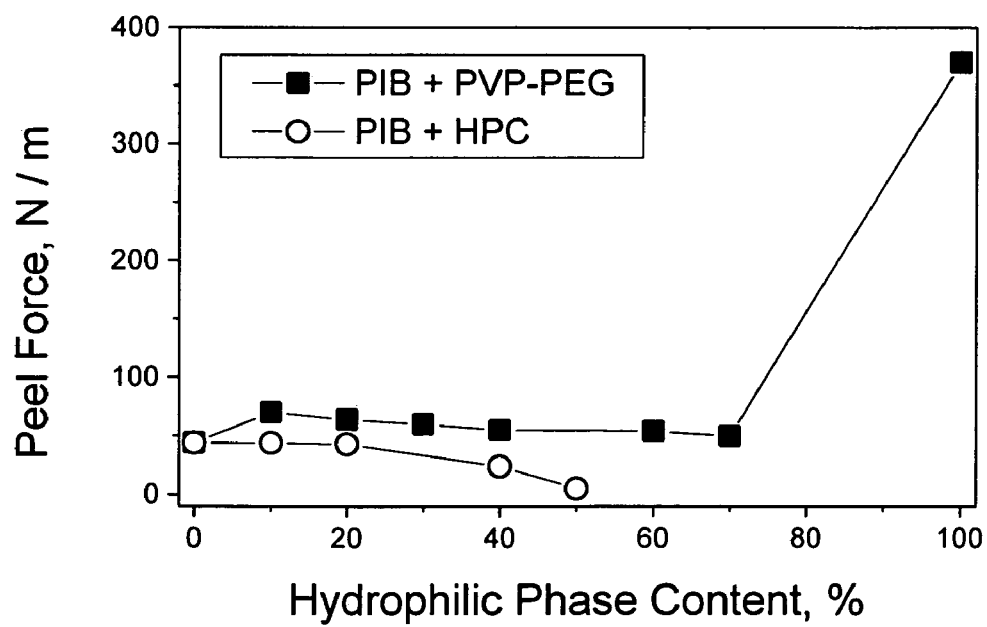
FIG. 10 shows the effect on the adhesion of PIB blends with PVP-PEG and HPC, as evaluated in Example 3.

Adhesive properties of PIB-BR blends with hydrophilic sorbents:

As shown in FIG. 10, mixing of a hydrophobic adhesive with 40% or more of a nonadhesive hydrophilic sorbent resulted in a gradual decrease of adhesion. If, however, the hydrophilic phase was the adhesive PVP-PEG hydrogel, the blending was not accompanied by a loss of adhesion. This trend was found to be typical of any hydrophobic adhesive and hydrophilic sorbent.

EXAMPLE 4

Effects of blending with hydrophilic sorbents on the viscoelastic behavior of hydrophobic adhesives:

To determine the viscoelastic properties of various two-phase adhesives, retardation analysis was employed, based on Equation 2:

$$J(t) = t_1/\eta_o + \sum_{1}^{i} J_i \cdot e^{[-(t-t_1)]/\lambda_i} \quad (2)$$

In this equation, the recovery response of a viscoelastic sample can be described in terms of the compliance $J(t)$, which is expressed as a function of retardation times $\lambda_i$, where $i=1, 2, 3$ etc., $\eta_0$ is an instantaneous dynamic viscosity (the material constant characterizing the resistance of a liquid against being forced to flow), and $t_i$ is a measurement time. For infinite time (t) all e-functions become zero and thus the equation reduces to $J(t=\infty)=t_i/\eta_0$, which equals the permanent strain, i.e. the amount of viscous squeezing flow of the sample. For $t_1=0$ and $J_{2,3...}=0$ the function (2) matches the Kelvin-Voigt model. The retardation analysis was performed using the Microcal Origin software with a three-term model $J_{eq}(t)=J_0+J_1+J_2$, where $J_{eq}(t)$ is the equilibrium retardation compliance (reciprocal of equilibrium retardation modulus).

The results, presented in Table 2, are in a close agreement with those obtained using the Kelvin-Voigt model. The present data are highly informative regarding the relaxation properties of the various components of the adhesive materials.

TABLE 2

Results of retardation analysis of several two-phase adhesives using Equation 2

| Composition | Squeezing force, N | $J_0$, Pa$^{-1}$ | $J_1$ | $J_2$ | $J_{eq}$ | $G_{eq}$, Pa | $\lambda_1$, sec | $\lambda_2$ |
|---|---|---|---|---|---|---|---|---|
| PIB-BR (1:1) + | 0.5 | | | | 5.94 10$^{-6}$ | 1.68 10$^5$ | 100 | |
| 5% APFR, | 1 | | | | 3.14 10$^{-6}$ | 3.19 10$^5$ | 106 | |
| uncured | 5 | | | | 6.27 10$^{-7}$ | 1.6 10$^6$ | 106 | |
| PIB-BR (1:1) + | 0.5 | | 8.3 10$^{-6}$ | 9 10$^{-6}$ | 1.73 1$^{-5}$ | 5.78 10$^4$ | 2.7 10$^{-10}$ | 213 |
| 5% APFR, | 1 | | 6.58 10$^{-6}$ | 3.43 10$^{-6}$ | 1 10$^{-5}$ | 1.10$^5$ | 1 10$^{-6}$ | 812 |
| cured | 5 | | 4.7 10$^{-6}$ | 1 10$^{-5}$ | 1.47 10$^{-5}$ | 6.8 10$^4$ | 268 | 1185 |
| PIB 70% + | 0.5 | | | | 8.53 10$^{-7}$ | 1.17 10$^6$ | 45 | |
| HPC 30% | 1 | | | | 4.67 10$^{-7}$ | 2.14 10$^6$ | 45 | |
| | 5 | | | | 3.17 10$^{-6}$ | 3.15 10 | 33 | |
| PIB − BR | 0.5 | 1.3 10$^{-12}$ | 7.65 10$^{-7}$ | 1.32 10$^{-6}$ | 2 10$^{-6}$ | 5 10$^5$ | 0.0001 | 124 |
| (40:60) + | 1 | 1.8 10$^{-24}$ | 3.87 10$^{-7}$ | 1.2 10$^{-6}$ | 1.6 10$^{-6}$ | 6.25 10$^{-5}$ | 11.27 | 250 |
| 30% − HPC | 5 | 1.9 10$^{-9}$ | 4.4 10$^{-7}$ | 3.5 10$^{-7}$ | 7.9 10$^{-7}$ | 1.26 10$^6$ | 30 | 540 |
| 50% (PIB | 0.5 | 4.61 10$^{-8}$ | 5.96 10$^{-6}$ | 5.38 10$^{-6}$ | 1.13 10$^{-6}$ | 8.82 10$^4$ | 42 | 611 |
| 30% + BR | 1 | 0 | 2.9 10$^{-6}$ | 3.6 10$^{-6}$ | 6.5 10$^{-6}$ | 1.5 10$^5$ | 160 | 955 |

TABLE 2-continued

Results of retardation analysis of several two-phase adhesives using Equation 2

| Composition | Squeezing force, N | $J_0$, Pa$^{-1}$ | $J_1$ | $J_2$ | $J_{eq}$ | $G_{eq}$, Pa | $\lambda_1$, sec | $\lambda_2$ |
|---|---|---|---|---|---|---|---|---|
| 40% + Regalite 30%) + 50% PVP-PEG (64/36) | 5 | 0 | | | 4.43 10$^{-7}$ | 2.26 10$^6$ | 564 | |

The low $J_0$ values found for the cured systems, and the blends containing HPC, are a sign of negligible flow contribution. It is important to note that HPC has been found to depress dramatically the squeezing flow of PIB and PIB-BR mixtures, whereas it has a weaker effect on other adhesives, e.g., DuraTak adhesives.

We claim:

1. A method for preparing a two-phase, water-absorbent bioadhesive composition comprising:
   (a) preparing a crosslinkable hydrophobic composition comprised of a hydrophobic polymer and at least one agent effective to crosslink the polymer; and
   (b) preparing a hydrophilic composition comprised of a hydrophilic polymer and a complementary oligomer capable of crosslinking the hydrophilic polymer through hydrogen bonding, ionic bonding, and/or covalent bonding;
   (c) admixing the crosslinkable hydrophobic composition with the hydrophilic composition; and
   (d) crosslinking the hydrophobic polymer in the admixture.

2. The method of claim 1, wherein the complementary oligomer is effective to crosslink the hydrophilic polymer in the presence of a curing agent.

3. The method of claim 2, wherein (d) further includes crosslinking the hydrophilic polymer.

4. The method of claim 3, wherein (d) is carried out at a temperature effective to thermally crosslink both the hydrophobic polymer and the hydrophilic polymer.

5. The method of claim 4, wherein the hydrophobic polymer is butyl rubber and the at least one agent comprises polyisobutylene.

6. The method of claim 5, wherein the at least one agent additionally comprises an organic peroxide.

7. The method of claim 4, wherein the curing agent is pentaerythritol monohydroxypentaacrylate.

* * * * *